US006426092B1

(12) United States Patent
Nitikhunkasem et al.

(10) Patent No.: US 6,426,092 B1
(45) Date of Patent: *Jul. 30, 2002

(54) POWDER COMPOSITIONS COMPRISING A SKIN IRRITATION REDUCING AGENT

(75) Inventors: Attaya Nitikhunkasem, Bangkok (TH); Alain V. Khaiat, Singapore (SG); John Hopkins, Newbury (GB)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/512,647

(22) Filed: Feb. 24, 2000

Related U.S. Application Data

(63) Continuation of application No. 09/208,322, filed on Dec. 9, 1998, now Pat. No. 6,048,549.
(60) Provisional application No. 60/068,262, filed on Dec. 19, 1997.

(51) Int. Cl.[7] .......................... A61K 9/14; A61K 31/35; A61K 31/205; A61K 31/045
(52) U.S. Cl. ....................... 424/489; 424/745; 514/455; 514/556; 514/729
(58) Field of Search ................................. 424/489, 405, 424/195.1; 514/455, 556, 729

(56) References Cited

U.S. PATENT DOCUMENTS

| | | | |
|---|---|---|---|
| 5,015,470 A | * | 5/1991 | Gibson |
| 5,266,592 A | * | 11/1993 | Grub et al. |
| 5,451,404 A | * | 9/1995 | Furman |
| 5,534,265 A | * | 7/1996 | Fowler et al. |
| 5,783,211 A | * | 7/1998 | Manzo et al. ................ 424/450 |
| 6,008,246 A | * | 12/1999 | Ito et al. ..................... 514/458 |

FOREIGN PATENT DOCUMENTS

| | | | |
|---|---|---|---|
| AU | 26111/77 | * | 12/1978 |
| AU | 79467/82 | * | 7/1982 |
| AU | 42800/85 | * | 11/1985 |
| AU | 70688/87 | * | 10/1987 |
| AU | 70690/87 | * | 10/1987 |
| AU | 70691/87 | * | 10/1987 |
| AU | 82175/87 | * | 6/1988 |
| AU | 10139/92 | * | 7/1992 |
| DE | 39 13 120 A1 | | 10/1990 |
| JP | 60-7962 | * | 4/1981 |
| JP | 62-10965 | * | 1/1982 |
| JP | 5-77644 | * | 2/1986 |
| JP | 4-47644 | * | 7/1986 |
| JP | 2628058 | * | 7/1989 |
| JP | 1-40002 | * | 8/1989 |
| KR | 93/10549 | * | 10/1993 |
| KR | 97/118867 | * | 10/1995 |
| WO | 87/05504 | * | 9/1987 |
| WO | 93/08793 | * | 5/1993 |
| WO | 83/17661 | * | 9/1993 |
| WO | 95/09635 | * | 4/1995 |
| WO | 96/11694 | * | 4/1996 |
| WO | 96/21719 | * | 7/1996 |
| WO | 96/22102 | * | 7/1996 |
| WO | 96/28008 | * | 9/1996 |

OTHER PUBLICATIONS

"Cool–A IPG," product brochure by Takasago International Corporation, 1995.*
"Betafin BPPC 10, Betaine anhydrous pharamceutical grade," product brochure by Finnfeeds Finland Ltd., 1998.*
"Phytoconcentrol camomile oil–soluble," product brochure by Dragoco, 1981.*
Evaluation, in vivo on human, of the anti–inflammatory effect of product C13 BO Natural Extract AP lot No. 65114231 versus placebo, Laboratoire Dermscan, 1996.*
"Ougon extract powder," product brochure, Ishimaru Pharcos Co., Ltd., 1997.*
"Ougon (Scutellara root extract)," product brochure, Ichimaru Pharcos Co., Ltd., 1997.*
"Questice, sloe release coolant," product brochure, Quest International, 1995.*
"FRESCOLAT cooling ingredients," product brochure, H&R, 1997.*
Database USPATFULL on STN, AN 91:38307, US 5015470 A (Gibson), bibliography and key words, May/1991.*
Database REGISTRY on STN, RN 107–43–7, 1–carboxy–N,N,N–trimethylmethanaminium hydroxide inner salt, 2000.*
Abstract: JP 8026969. Yuchi Izumi, dated Jan. 30, 1996 for "Cosmetic Composition".
Abstract: JP 9157172. Yanagibashi Norio, dated Jun. 17, 1997, for "Skin External Agent and Treating Agent for Eczema".
Abstract: JP 63033326 A. Saeki Kuniko, dated Feb. 13, 1998 for "Antibacterial Composition".
Abstract: CN 1100954A, Wang, 1995, for "Pearl Powder for Curing Bedsore".
Abstract CN1110581, Oct. 25, 1995. Topical Chinese herbal Decoction for Treating e.g. Bed Sore, Zhang.
Abstract HU19900005313, Aug. 24, 1990, Spinach Extract as an Active Ingredient in Cosmetic Product, Biogal Gyogyszergyar (BIOG).

* cited by examiner

Primary Examiner—Minna Moezie
Assistant Examiner—Alysia Berman
(74) Attorney, Agent, or Firm—Michele G. Mongini; Erin M. Harriman

(57) ABSTRACT

A novel powder composition comprised of a skin irritation reducing agent comprising 1-Carboxy-N,N,N-trimethylmethanaminium hydroxide inner salt, scutellaria baicalensis extract, bisabolol, or mixtures thereof. Also provided is a method for treating prickly heat comprised of topically applying an effective amount of the powder to a desired area.

4 Claims, No Drawings

POWDER COMPOSITIONS COMPRISING A SKIN IRRITATION REDUCING AGENT

CROSS REFERENCE TO RELATED APPLICATION

This application, is a continuation application of U.S. application Ser. No. 09/208,322 filed Dec. 9, 1998, now U.S. Pat. No. 6,048,549 which claims the benefit of U.S. Provisional Application No. 60/068,262, filed on Dec 19, 1997, which is incorporated by reference in its entirety.

BACKGROUND OF THE INVENTION

1. Field of the Invention

The present invention relates to a novel powder composition. More particularly, this invention relates to a novel powder composition having improved anti-microbial, cooling and skin soothing properties.

2. Description of the Prior Art

Miliria Rubra, commonly known as "prickly heat", is a skin condition that results from an obstruction of the sweat gland ducts. More specifically, keratin plugs are formed due to the maceration of the stratum corneum accompanied by the distension of the sweat gland ducts. Prickly heat may be identified by the development of an intensely itchy rash on the skin that is composed of small vesicles, and may also be accompanied by a secondary bacterial infection. Babies often develop prickly heat, in particular during periods of warmer weather.

Several known methods exist for treating prickly heat and the symptoms thereof. One such method is the application of a powder mixture consisting of talc with one or more antibacterial agents such as boric acid, salicylic acid, and chlorphenesin. Disadvantageously, such treatments are inappropriate for use on babies' skin because the antibacterial agents tend to irritate the skin and because of the concern over the toxicity effects that may be associated with the use of such antibacterial agents.

It would be desirable to develop a powder composition that was effective in treating the symptoms of prickly heat, but that was also safe for use on babies' skin.

SUMMARY OF THE INVENTION

In accordance with this invention, there is provided a novel powder composition comprised of, consisting of, and/or consisting essentially of, based upon the weight of the composition, a skin irritation reducing agent comprising 1-Carboxy-N,N,N-trimethylmethanaminium hydroxide inner salt, scutellaria baicalensis extract, bisabolol, or mixtures thereof.

Another embodiment of the invention is directed to a method for treating prickly heat comprised of, consisting of, and/or consisting essentially of topically applying an effective amount of a powder comprised, consisting of, and/or consisting essentially of a skin irritation reducing agent comprising 1-Carboxy-N,N,N-trimethylmethanaminium hydroxide inner salt, scutellaria baicalensis extract, bisabolol, or mixtures thereof.

The powders of this invention exhibit one or more beneficial properties. Not only do the powders relieve the symptoms of prickly heat by providing antimicrobial, soothing, and cooling benefits to the skin, but they also do so without the use of harsh antimicrobial agents which tend to irritate sensitive skin.

DESCRIPTION OF THE PREFERRED EMBODIMENTS

The main component of the powder composition of the present invention is a skin irritant reducer. Suitable skin irritant reducers include, but are not limited to 1-Carboxy-N,N,N-trimethylmethanaminium hydroxide inner salt, which is also known as trimethylglycine (betaine), scutellaria baicalensis extract, bisabolol, and mixtures thereof. One suitable mixture includes bisabolol, soybean oil, and chamomile extract and is available from Dragoco, Ltd. under the tradename, "Phytoconcentrol Chamomile."

1-Carboxy-N,N,N-trimethylmethanaminium hydroxide inner salt, which is an amino acid extracted from sugar beets that is commercially available from Cultor Ltd. (Finnsugar Bioproduct) under the tradename, "BETAFIN BPP", may be used in the powder composition of the present invention in an amount, based upon the total weight of the composition, from about 0.005% to about 50%, preferably from about 0.05% to about 10.0%, and more preferably from about 0.1% to about 5.0%.

Scutellaria baicalensis extract, which is derived from the root of the Scutellaria baicalensis georgi plant and is commercially available from Ichimaru Pharcos Co., Ltd. under the tradename, "Ougon Exatract Powder," may be used in the powder composition of the present invention in an amount, based upon the total weight of the composition, from about 0.00001% to about 0.10%, preferably from about 0.0001% to about 0.08%, and more preferably from about 0.001% to about 0.05%.

Bisabolol, which is available from Dragoco, Ltd. under the tradename "DRAGOSANTOL," may be used in the powder composition of the present invention in an amount, based upon the total weight of the composition, from about 0.1% to about 2.0%, preferably from about 0.15% to about 1.5%, and more preferably from about 0.2% to about 0.5%.

Several other components may be present in the powder composition of the present invention such as a base including, but not limited to talc, cornstarch, and mixtures thereof. Talc is preferred. Preferably the base is sterilized via methods well known in the art such as via steam sterilization. before it is combined with the other ingredients of the powder of the present invention. Suitable amounts of talc may range from, based upon the total weight of the powder composition, about 50% to less than about 100%, preferably from about 70% to about 99%, and more preferably from about 80% to about 99%.

Another component that may be present in the powder composition of the present invention is a cooling agent that includes but not is not limited to menthol; eucalyptus oil; peppermint oil; cyclohexanol, 5-methyl-2-(1-methylethenyl)-, available from Takasago International Corporation, Tokyo under the tradename, COOLACT; 6-Isopropyl-9-methyl-1,4-dioxaspiro-(4,5)decane-2-methanol, (I)-menthone glycerol ketal (Menthone Glycerin Acetal) available from Haarmann & Reimer ("H&R") under the tradename, FRESCOLAT MGA; 5-methyl-2-(1-methyl ethyl)-cyclohexyl-2-hydroxypropionate, I-menthyl lactate, acid/-menthyl ester (Menthyl Lactate) available from H&R under the tradename, FRESCOLAT ML; menthyl pyrrolidone carboxylate (Menthyl PCA) available from Quest International UK Limited under the tradename, QUESTICE, and mixtures thereof. The cooling agent may be used in an amount, based upon the total weight of the powder composition, of from about 0.01% to about 0.50%. Preferably, the menthol may be used in an amount, based upon the total weight of the composition, from about 0.01% to about 0.50%, more preferably from about 0.05% to about 0.30%, and most preferably from about 0.10% to about 0.20% and the eucalyptus oil and peppermint oil, respectively, may be used in an amount, based upon the total weight of the composition, from about 0.01% to about 0.50%, more preferably from about 0.05% to about 0.40%, and most preferably from about 0.20% to about 0.30%. The menthol and the eucalyptus oil provide a fresh, cooling feeling to the user. A mixture of menthol and eucalyptus oil is the preferred coolant.

Another component that may be used in the powder composition of the present invention is an astringent. Suitable astringents include, but are not limited to zinc oxide, glyoxyl diureide available from Sutton Laboratories under the trade name, "ALLANTOIN," and mixtures thereof. The astringents may be used in an amount, based upon the total weight of the composition, from about 0.10% to about 10.0%, preferably from about 0.5% to about 5.0%, and more preferably from about 0.5% to about 3.0%. Zinc oxide is preferred due to its mild antiseptic and astringent properties.

Another component of the present invention may be an antimicrobial agent comprised of benzethonium chloride, (-p-Chloro-3, 5-m-xylenol)("PCMX")(also known as "chloroxylenol"), and mixtures thereof. The preferred antimicrobial agent is PCMX. In one preferred embodiment, PCMX is used in combination with bisabolol skin irritant reducing agent. The amount of antimicrobial agent used in the composition of the present invention may range from about 0.10% to about 5.0%, preferably from about 0.2% to about 3.0%, and more preferably from about 0.3% to about 1.0%. Chloroxylenol (-p-Chloro-3, 5-m-xylenol), which is commercially available from Nipa Laboratories Ltd. under the tradename, NIPACIDE PX, is preferred for its unique combination of nontoxic antimicrobial and preservative properties.

In addition to the above components for the powder composition, the composition may include other optional components including, but not limited to, anticaking agents, absorbing agents, water-repellent agents, perfumes, vitamins, and mixtures thereof.

Suitable anti-caking agents include, but are not limited to tribasic calcium phosphate, silicon dioxide, kaolin, hydrated aluminum silicate, and mixtures thereof, and suitable absorbing agents include, but are not limited to magnesium carbonate available from Konoshima Chemical Co. Ltd. under the tradename, "MAGNESIUM CARBONATE LIGHT." Suitable water-repellent agents include, but are not limited to magnesium stearate. The anti-caking agents, absorbing agents and water-repellent agents may be used in an amount, based upon the total weight of the composition, of from about 0.1% to about 15%, and preferably from 0.5% to about 10%.

The perfume may be present in an amount, based upon the total weight of the powder composition, of from about 0.05% to about 1%, and preferably from about 0.1% to about 0.5%.

Suitable vitamins include, but are not limited to vitamin E, D-Panthenol (also known as "Provitamin B5"), and mixtures thereof, and may be present in an amount, based upon the total weight of the powder composition, of from about 0.01% to about 5.0%, and preferably from about 0.05% to about 2%.

The powder composition of the present invention may be made by combining the components in any mixing device well-known in the art, including, but not limited to any type of powder blender, with a ribbon mixer being most preferred. The components are preferably combined under pressure conditions of about 14.7 psi (atmospheric pressure), and a temperature of about 20° C. to about 32° C., and preferably from about 25° C. to about 28° C.

In a preferred embodiment, the desired amounts of menthol, eucalyptus oil, and chloroxylenol are dissolved in the perfume of choice under a temperature of from about 20° C. to about 32° C., and preferably from about 25° C. to about 28° C. in any of the above-mentioned conventional mixers until this first mixture is homogeneous. Alternatively, in another embodiment, the desired amounts of menthol, eucalyptus oil and chloroxylenol may be premixed in a conventional mixer such as a stainless steel bin with a mechanical stirrer under ambient conditions until the first premixed mixture is homogeneous before being dissolved in the perfume. The mixers are preferably made of corrosion resistant material such as glass or stainless steel. Pressure is not critical, although convenient operating pressures may range from about 14 psi to about 15 psi.

In another mixing device, an effective amount of the scutellaria baicalensis extract, zinc oxide, betaine, and, based upon the total weight of the base used in the powder composition of the present invention, from about 5% to about 20%, and preferably from about 7% to about 15% of talc are mixed under temperature conditions of from about 20° C. to about 32° C., and preferably from about 25° C. to about 28° C. in any of the above-mentioned conventional mixers until the resulting second premixed mixture is homogeneous. A ribbon mixer is preferred. Pressure is not critical, although convenient operating pressures may range from about 14 psi to about 15 psi.

The second premixed mixture is mixed with the remaining amount of talc in a conventional mixer under until the resulting third mixture is homogeneous. Temperature and pressure are not critical; however convenient operating temperatures may range from about 20° C. to about 35° C. and operating pressures may range from about 14 psi to about 15 psi. The first premixed mixture is then added, preferably via spraying with a conventional spraying device such as a Mateer-Burt sprayer, into the third mixture and mixed under similar temperature and pressure conditions until the resulting mixture is homogeneous.

The invention illustratively disclosed herein suitably may be practiced in the absence of any component, ingredient, or step which is not specifically disclosed herein. The examples are set forth below to further illustrate the nature of the invention and the manner of carrying it out. However, the invention should not be considered as being limited to the details thereof.

EXAMPLES

Example 1

Preparation of Premix 1

0.15 kg of menthol, 0.25 kg of eucalyptus oil, and 0.1 kg of p-chloro-3,5-m-xylenol available from Nipa Laboratories Ltd. under the tradename, "Nipacide PX" were dissolved in 0.18 kg of perfume available from Givaudan-Roure Ltd. under the tradename, "Parfex 46109" under a temperature of 25 to 30° C. and atmospheric pressure in a steel bin having a mechanical stirrer. The mixture was mixed at a speed of about 25 revolutions/minute for about 10 minutes until the resulting mixture was homogeneous.

Example 2

Preparation of Premix 2

0.005 kg of *Scutellaria baicalensis* Extract available from Ichimaru Pharcos Co., Ltd. under the tradename, "Ougon Extract Powder," 0.5 kg. of 1-Carboxy-N,N,N-trimethylmethanaminium hydroxide inner salt available from Cultor Ltd. under the tradename, "Betafin BPP," and about 1 kg of zinc oxide were mixed with 10 kg of talc under ambient conditions in a 37 SC model Mateer-Burt ribbon mixer for about 12 minutes at a speed of about 25 revolutions/minute until the resulting mixture was homogeneous.

Example 3

Preparation of Powder Composition

The product of Example 2 was mixed with 88 kg of talc in a large 37 SC model Mateer-Burt ribbon mixer under ambient conditions for about 10 minutes at a speed of about 25 revolutions/minute to form a homogeneous mixture. After spraying in the product of Example 1 into the homogeneous mixture via a 37 SC model Mateer-Burt sprayer at a volumetric rate of about 0.07 kg/min for a period of about 8 minutes, the resultant mixture is further mixed in the same mixer under ambient conditions at a speed of about 28 revolutions/minute for about 40 minutes until the resulting powder was homogeneous.

Example 4

Consumer Testing of Powder Composition

Samples of the powder produced in Example 3 were given to 28 babies and samples of Johnson's™ Baby Prickly Heat Powder were given to 32 other babies, all of which possessed symptoms of prickly heat rash. The latter does not possess either *Scutellaria baicalensis* extract or 1-Carboxy-N,N,N-trimethylmethanaminium hydroxide inner salt, but instead includes about 200 g. of 0.2% Chamomile Oil. About 93% of the participants were classified as having mild to moderate rashes and about 7% of the participants were classified as having more severe rashes.

The parents were instructed to apply the powder to the affected area(s) on their babies after such area(s) were washed and patted dry for a minimum of at least two times a day for 10 consecutive days. After the ten-day period, 96.9% of the rashes on babies who used the Johnson's™ Baby Prickly Heat powder and 92.9% of the rashes on babies who used the powder of Example 3 were improved. More specifically, for babies who used the powder of Example 3, 92.8% of the participants reported that the rashes improved after only 5 days of treatment and further improved/cleared after 10 days of treatment. Similarly, 96.87% of those using the Johnson's™ Baby Prickly Heat powder reported an improvement in the rashes after 5 days of treatment and further improvement/clearing after 10 days of treatment.

This Example shows that the claimed powder composition effectively clears and prevent the symptoms of prickly heat rash. Since many of the participants had rashes over multiple areas of their bodies, this Example shows that the powder compositions were effective in treating the rashes independent of the location or number of body sites affected.

We claim:

1. A powder composition, comprising:
   (1) a base selected from talc, cornstarch or mires thereof;
   (2) from about 0.01% to about 0.50% of menthol;
   (3) from about 0.01% to about 0.50% of eucalyptus oil;
   (4) from about 0.10% to about 10% of zinc oxide;
   (5) from about 0.005% to about 50% of 1-carboxy-NN,N-trimethylmethanaminium hydroxide inner salt;
   (6) from about 0.00001% to about 0.10% of *Scutellaria baicalensis* extract; and
   (7) from about 0.10% to about 5.0% of chloroxylenol all percents based on the total weight of the composition.

2. A method for treating prickly heat in a human comprised of topically applying to the skin of said human an effective amount of the powder composition of claim 1.

3. A method according to claim 2, wherein the *Scutellaria baicalensis* extract is present in an amount, based upon the total weight of the composition, from about 0.0001% to about 0.10%.

4. A method according to claim 3, wherein the *Scutellaria baicalensis* extract is present in an amount, based upon the total weight of the composition, from 0.001% to about 0.08%.

* * * * *